United States Patent
Ross et al.

(10) Patent No.: US 6,444,470 B1
(45) Date of Patent: Sep. 3, 2002

(54) TRANSFORMATION-ENHANCING COMPOSITIONS AND METHODS OF USE

(75) Inventors: Margit C. Ross, Johnston; Laura A. Church; William J. Gordon-Kamm, both of Des Moines, all of IA (US)

(73) Assignee: Pioneer Hi-Bred International, Inc., Des Moines, IA (US)

(*) Notice: Subject to any disclaimer, the term of this patent is extended or adjusted under 35 U.S.C. 154(b) by 0 days.

(21) Appl. No.: 09/425,510

(22) Filed: Oct. 22, 1999

(51) Int. Cl.$^7$ ............................ C12N 15/82; C12N 5/04; C12N 5/10; C12N 15/87; A01H 4/00
(52) U.S. Cl. ...................... 435/468; 435/412; 435/419; 435/430; 435/430.1; 435/424; 435/431; 800/278; 800/298; 800/320.1
(58) Field of Search .................. 800/278, 298, 800/320.1, 320.3, 320.2, 320, 312, 322, 317.2, 314; 435/419, 424, 468, 430.1, 431, 430, 412

(56) References Cited

U.S. PATENT DOCUMENTS 6,140,555 A * 10/2000 Reichert et al.

OTHER PUBLICATIONS

Ma et al., "Stem Infusion of Field–Grown Maize", *Commun. Soil Sci. Plant Anal.* 25(11&12) 2005–2017 (1994).
Ma et al., "Stem–Infused Nitrogen–15 Enrichment for Evaluation of Nitrogen Use in Maize", *Commun. Soil Sci. Plant Anal.* 29(15&16) 2459–2470 (1998).
Lur et al., "Role of Auxin in Maize Endosperm Development", *Plant Physiol.* 103:273–280 (1993).
Boyle et al., "Stem Infusion of Maize Plants", *Crop Science* 31:1241–1245 (1991).
Boyle et al., "Stem Infusion of Liquid Culture Medium Pervents Reproductive Failure of Maize at Low Water Potential", *Crop Science* 31:1246–1252 (1991).
Zhou et al., "A New Technique for Continuous Injection into Stems of Field–Grown Corn Plants",*Crop Science* 452–456 (1996).
Zinselmeier et al., "Starch and the Control of Kernel Number in Maize at Low Water Potentials", *Plant Physiol.* 121:25–35 (1999).
Zinselmeier et al., "Reversing Drought–Induced Losses of Grain Yields: Sucrose Maintains Embryo Growth in Maize", *Crop Science* 35:1390–1400 (1995).
Dietrich et al., "Changes in cytokinins and cytokinin oxidase activity in developing maize kernels and the effects of exogenous cytokinin on kernel development", *Plant Physiol Biochem.* 33(3):327–336 (1995).
Lukaszewski et al., "Asparagine and Boric Acid Cause Allantoate Accumulation in Soybean Leaves by Inhibiting Manganese–Dependent Allantoate Amidohydrolase", *Plant Physiol.* 99:1670–1676 (1992).
Serraj et al., "Involvement of Ureides in Nitrogen Fixation Inhibition in Soybean", *Plant Physiol.* 119:289–296 (1999).
Grabau et al., "Stem Infusion Enhanced Methionine Content of Soybean Storage Protein", *Plant Physiol.* 82:1013–1018 (1986).
Grabau et al., "P Nutrition during Seed Development", *Plant Physiol.* 82:1108–1012 (1986).
Tarpley et al., "Internodal Compartmentation of Stem–Infused [$^{14}$C]Sucrose in Sweet and Grain Sorghum", *Crop Science* 34:1116–1120 (1994).
Bashor et al., "Effects of exogenous application and stem infusion of ascorbate on soybean (*Glycine max*) root nodules", *New Phytol.* 142:19–26 (1999).
Dong J. et al. An improved procedure for production of transgenic flax plants using Agrobacterium tumefaciens. Plant Science 88:61–71, 1993.*
Salisbury F.B. and C.W. Ross. Plant Physiology (Second Edition). Wadsworth Publishing Co. Inc., Belmont, CA. 1978. pp. 264 and 271.*
Hansen et al, Recent advances in the transformation of plants, Jun. 1999, Trends in Plant Science (Reviews), vol. 4, No. 6, pp. 226–230.*

* cited by examiner

Primary Examiner—David T. Fox
Assistant Examiner—David H. Kruse
(74) Attorney, Agent, or Firm—Pioneer Hi-Bred International, Inc.

(57) ABSTRACT

The invention relates to compositions and methods and for genetically transforming *Zea mays* plants. Compositions comprising transformation-enhancing agents and methods of use are provided. The methods involve administering an effective amount of a transformation-enhancing agent to a *Zea mays* plant. The compositions and methods of the invention find use in improving transformation efficiency and increasing the embryogenic response of callus.

24 Claims, No Drawings

TRANSFORMATION-ENHANCING COMPOSITIONS AND METHODS OF USE

FIELD OF THE INVENTION

The present invention relates to the field of genetic engineering. The invention further relates to increasing the embryogenic response of callus, transforming plant cells and regenerating plants from cells and tissues.

BACKGROUND OF THE INVENTION

The development of methods for the introduction of foreign genes into organisms has had a profound impact on fields of medicine and agriculture. While the movement of genes within plant species or between closely related plant species by traditional methods based on sexual reproduction has played an important role in crop improvement for most of this century, the pace of crop improvement by such methods has been slow and limiting due to the reliance on naturally occurring genes. Recent advances in the field of genetic engineering has led to the development of genetic transformation methods that allow the introduction of recombinant DNA, into organisms. The recombinant DNA methods which have been developed have greatly extended the sources from which genetic information can be obtained for crop improvement. Recently, new crop plant varieties, developed through recombinant DNA methods, have reached the marketplace. Genetically engineered soybeans, maize, canola and cotton are now widely utilized by North America farmers.

Rapid progress has been made in developing the tools for manipulating genetic information in plants. Plant genes are being cloned, genetic regulatory signals deciphered, and genes transferred from entirely unrelated organisms to confer new agriculturally useful traits to crop plants. Recombinant DNA methods significantly increase the gene pool available for crop improvement. A variety of methods have been developed for the transformation of plants and plant cells with DNA.

Cereals comprise a commercially valuable group of plant species that could benefit from the introduction and expression of foreign genes controlling improved grain quality and such agronomically important traits as tolerance to disease, insects, herbicides, and stress. The use of microprojectile-bombardment-mediated transformation of embryogenic tissue culture material, with the subsequent regeneration of transgenic plants, has overcome the regeneration problems associated with the production of plants from cereal protoplasts. Using this technology, transgenic plants have been obtained from microprojectile-bombarded tissue cultures of many species.

Many of the recent advances in plant science have resulted from application of the analytical power of recombinant DNA technology coupled with plant transformation. These approaches facilitate studies of the effects of specific gene alterations and additions on plant development and physiology. They also make possible the direct manipulation of genes to bio-engineer improved plant varieties.

While strides have been made in the genetic transformation of plants, it is by no means a routine matter. For many important crop plants, the efficiency of transformation as measured by the number of transformed plants recovered per transformation attempt is very low and highly variable from one genetic line or variety to the next. Often, highly desirable breeding lines exhibit extremely low transformation efficiencies, relative to other genetic lines of the same crop species. Frequently, acceptable levels of transformed plant cells and calli can be obtained from a transformation attempt but such transformed plant cells and calli are recalcitrant to regeneration into transformed embryos and plants. While some success has already been achieved in improving crop plants through the introduction of recombinant DNA, the progress of genetic engineers working to improve many important crop species is impeded by inefficient methods for transforming and regenerating crop plants. Thus, improved methods for transforming plant cells and regenerating transformed plants are desired.

SUMMARY OF THE INVENTION

Methods and compositions are provided for preparing plants for transformation, producing transformed plants and plant embryos and increasing plant transformation efficiency. The methods involve administering to a plant an effective amount of a transformation-enhancing agent prior to attempting to transform a cell from the plant. The transformation-enhancing agent comprises one or more components that when administered to a plant increases transformation efficiency when cells from the plant are subsequently used in plant transformation methods. The compositions comprise a transformation-enhancing agent and a carrier. The methods and compositions of the invention find use in agriculture, particularly in transforming crop plants, more particularly in transforming crop plants that display low transformation efficiencies with existing transformation methods.

Also provided are transgenic plants and seeds thereof.

DETAILED DESCRIPTION OF THE INVENTION

A number of terms used herein are defined and clarified in the following section.

By "increase transformation efficiency" is intended that the number of transformed plants recovered from a transformation attempt is increased preferably at least two fold, preferably at least five fold, more preferably at least ten fold.

By "transformation-enhancing agent" is intended a composition that when applied to a plant prior to and/or during a transformation attempt increases transformation efficiency. Such a "transformation-enhancing agent" may favorably influence one of more of the physiological processes associated with genetic transformation and the subsequent regeneration of transformed plants including, but not limited to, foreign DNA uptake into plant cell, foreign DNA integration in a genome of a plant cell, plant cell proliferation in culture, plant cell culture initiation, proliferation of transformed plant cell, embryogenesis, shoot initiation and root initiation.

By "effective amount of a transformation-enhancing agent" is intended an amount that favorably affects one or more of processes associated with increasing transformation efficiency including, but not limited to, uptake of foreign DNA by a cell, integration of foreign DNA into the genome of a cell, expression of a foreign gene in a transformed cell, proliferation of a transformed cell, callus formation, embryogenesis, root formation and shoot formation. Those of ordinary skill in the art understand that such an "effective amount" depends on a number of factors including, but not limited to, the transformation-enhancing agent employed, the species of plant, the developmental stage of the plant, the method by which the transformation-enhancing agent is administered, environmental conditions and the type of cells to be transformed.

The invention is drawn to compositions and methods for genetically transforming plant cells and regenerating transformed plants. The compositions and methods find use in improving existing methods for producing transformed plants, particular transformed crop plants, more particularly transformed monocot crop plants, most particularly transformed maize plants. The compositions comprise transformation-enhancing agents. When administered to a plant in an effective amount prior to a transformation attempt, such transformation-enhancing agents increase transformation efficiency.

Compositions comprising a transformation-enhancing agent are provided. Additionally, compositions comprising a transformation-enhancing agent and a carrier are provided. The compositions increase transformation efficiency when applied to a plant prior to a transformation attempt. While such transformation-enhancing agents do not depend on any particular biological mechanism for increasing transformation efficiency, it is recognized that the transformation-enhancing agents may alter one or more processes such as, for example, uptake of foreign DNA by a cell, integration of foreign DNA into the genome of a cell, expression of a foreign gene in a transformed cell, proliferation of a transformed cell, cell division, callus formation, embryogenesis, root formation, shoot formation and leaf formation. The transformation-enhancing agents of the invention may affect any one or more of the structures, mechanisms or processes of a plant in such a manner that transformation efficiency is increased.

In addition, the transformation-enhancing agents find use in the initiation, growth and differentiation of cultures of plant cells and plant tissues. Such cultures may be comprised of plant cells that are genetically transformed, untransformed or both. The transformation-enhancing agents may enhance one or more desired processes associated with cultures of plant cells and plant tissues including, but not limited to, cell culture initiation, cell proliferation, callus formation, embryogenesis, differentiation, shoot formation, leaf formation and root formation.

As indicated the methods of the invention find use in improving transformation efficiency, particularly with plants known to be recalcitrant to transformation and regeneration by existing methods, more particularly grain and oilseed plants, most particularly maize. The methods involve administering an effective amount of a transformation-enhancing agent of the invention to a plant, plant tissue or cell prior to a transformation attempt. Such a transformation-enhancing agent increases transformation efficiency when cells from such a plant are subsequently used in a transformation attempt. The methods further comprise transforming-a cell from such a plant with a nucleotide sequence of interest and regenerating a transformed plant.

Generally, an effective amount of a transformation-enhancing agent may be determined by administering an amount of the transformation-enhancing agent of the invention to a first plant and transforming cells from the plant with a DNA construct. For comparison, cells from a second plant, referred to as a control plant, to which the transformation-enhancing agent was not administered are transformed with the same DNA construct at approximately the same time. Typically the results of such transformation attempts are indicated as the number of transformed cells, calli, embryos or plants. A comparison of the results achieved with cells from the first and second plants is used to determine whether the amount of the transformation-enhancing agent administered is an effective amount. By such an approach, an effective amount of a transformation-enhancing agent is an amount sufficient to, provide an increased number of transformed cells, calli, embryos or plants when administered to a plant, relative to the number of transformed cells, calli, embryos or plants achieved with a control plant.

Preferred embodiments of the invention comprise administering a transformation-enhancing agent to a plant prior to contacting the plant or any cells thereof with a DNA construct of the invention or with a bacterium harboring such a DNA construct. The transformation-enhancing agent or composition may be administered to a plant by any means such as, for example, external application to the plant body in sprays, drips, mists, powders, dusts, vapors or gases, injecting the plant or any part thereof, soil application and application in irrigation water.

The transformation-enhancing agents may be administered to a specific part of the plant body. Such a specific part of the plant body may contain the desired cells for transformation with the DNA construct of the invention. Alternatively, the transformation-enhancing agents or compositions may be administered to a part of the plant body which does not contain the desired cells for transformation to achieve an increase in transformation efficiency. Such an increase in transformation efficiency may result from active or passive transport or diffusion of the transformation enhancing agent to the desired cells for transformation. Alternatively, the transformation-enhancing agent may affect cells in the region where the transformation-enhancing agent was administered resulting in the affected cells initiating or facilitating in some manner one or more structural or physiological changes in the plant that lead to an increase in transformation efficiency in the desired cells for transformation.

In a first embodiment of the invention, methods are provided for transforming a plant involving administering a transformation-enhancing agent to a plant following pollination of the plant, preferably a grain or oilseed plant, more preferably a grain plant, most preferably a maize plant. The methods further involve transforming cells from an embryo produced by the plant with a DNA construct comprising a nucleotide sequence of interest and regenerating a stably transformed plant from such transformed cells.

In exemplary methods of the first embodiment, the transformation-enhancing agent is administered to a maize plant between 0 and 8 days after pollination of the maize plant, the pollinated ear from the maize plant is harvested 1 to 5 days later, and the harvested ear is used as a source of immature embryo cells for transformation. Preferred transformation-enhancing agents include dicamba, hormone cocktail, ABA, proline mix, liquid callus initiation medium, 2,4-D, salts cocktail 1 and 2,4-D+salts cocktail 1.

Preferably, the transformation-enhancing agent is administered to the ear or a part of the plant that allows the transformation-enhancing agent to enter the region of the immature embryos in an ear. The transformation-enhancing agent may be administered directly to the immature kernels containing the immature embryos. To administer the agent, a needle attached to a syringe is carefully placed through the husk leaves into the air space at the base of the ear and the agent is injected.

Alternatively, the transformation-enhancing agent may also be administered in a lanolin paste to the husks surrounding the ear or directly to the pericarp of the developing kernels. For administration to the pericarp, the husks surrounding the ear may be carefully and non-destructively separated from the immature kernels. The transformation-enhancing agent is combined with lanolin and administered directly to the pericarp of kernels. The husks are subsequently returned to their original position.

The transformation-enhancing agent may also be delivered to the immature embryos by administering the agent to a part of the plant that is a photosynthate source for the developing ear, such as, for example, a subtending leaf of the ear, or to a part of a plant that is involved in delivering photosynthate to the developing ear, such as, for example, phloem.

Methods of the invention are useful for increasing plant transformation efficiency. The methods find use in increasing the recovery of transformed plant cells and transformed plants from a transformation attempt. The methods may be used with any methods for transforming plants known to those of ordinary skill in the art including, but not limited to, Agrobacterium-mediated methods and biolistic methods. The methods of the present invention involve administering to a plant an effective amount of a transformation-enhancing agent of the invention, transforming a cell from the plant with a DNA construct comprising a nucleotide sequence of interest, and regenerating the cell into a transformed plant.

In second embodiment of the invention, methods are provided for increasing the transformation efficiency of maize transformation. The methods comprise administering an effective amount of a transformation-enhancing agent of the invention to a maize plant. Preferably, the transformation-enhancing agent is administered to the plant in such a manner that the transformation-enhancing agent enters the region of the maize plant containing the desired maize cells for transformation, particularly embryo cells. Such desired maize cells may be subsequently transformed by any method of maize transformation to increase the number of maize plants recovered from a transformation attempt.

Methods are provided for preparing a plant for a transformation attempt. The methods find use in increasing the number of transformed cells, transformed adventitious shoots, transformed embryos or transformed plants recovered from a subsequent transformation attempt. The methods involve administering to a plant an effective amount of a transformation-enhancing agent of the invention. Preferably, such a transformation-enhancing agent is administered to the plant, or any part, organ, tissue or cell thereof, before the desired cells for transformation are contacted with the DNA construct of the invention or with a bacterium harboring such a DNA construct.

In a third embodiment of the invention, methods are provided for preparing a crop plant for a transformation attempt. The methods of the present may be employed to prepare a plant for subsequent use in any existing method for transforming a crop plant. Preferably, the crop plant is a grain plant. More preferably, the crop plant is selected from the group consisting maize, sorghum, wheat, rice, rye and barley. Most preferably, the crop plant is maize. The methods involve administering an effective amount of a transformation enhancing agent to a crop plant. Preferably, the transformation-enhancing agent is administered to the plant in the vicinity of the desired cells for use in a subsequent transformation attempt. Alternatively, the transformation-enhancing agent may be administered to the plant in a region distal to the region containing such desired cells for transformation. The transformation-enhancing agent is administered to the crop plant before the using such desired cells in a transformation attempt. Preferably, the transformation-enhancing agent is administered between 0 and 8 days after pollination of the maize plant. The pollinated ear from the maize plant is harvested 1 to 5 days later to use such desired cells in a transformation attempt.

Methods are provided for transforming plant embryos. Such methods find use in providing a source of transformed embryos and transformed shoots that may be used to produce transformed plants. The methods of the invention encompass all transformed shoots including, but not limited to, transformed adventitious shoots and transformed shoots that originate from an apical meristem. The transformed embryos or transformed shoots may be used to produce transformed plants by any methods known to those of ordinary skill in the art. The methods of the invention comprise administering an effective amount of a transformation-enhancing agent to a plant. Such a transformation-enhancing agent increases the recovery of transformed embryos or transformed shoots from a transformation attempt. That is, the number of transformed embryos or transformed plants is increased. The methods further comprise transforming a cell from a natural embryo produced by the plant with a DNA construct comprising a nucleotide sequence of interest and regenerating the cell into a transformed embryo or transformed shoot.

In another embodiment the invention provides methods for increasing the embryogenic response of callus. The methods employ administering an effective amount of a transformation-enhancing agent to a plant and exposing a cell from an embryo produced by said plant to a callus media. Preferably, the callus media is 604 or 560P. Preferably, the transformation-enhancing agent is administered to the plant in the vicinity of the desired cells for use in a subsequent transformation attempt. Alternatively, the transformation-enhancing agent may be administered to the plant in a region distal to the region containing such desired cells for transformation. The transformation-enhancing agent is administered to the crop plant before the using such desired cells in a transformation attempt. Preferably, the transformation-enhancing agent is administered between 0 and 8 days after pollination of the maize plant. The pollinated ear from the maize plant is harvested 1 to 5 days later to use such desired cells in a transformation attempt.

Preferred embodiments of the invention involve transformation of cells derived from an immature embryo, particularly cells from immature cereal embryos, more particularly scutellar and meristem cells from an immature cereal embryo, most particularly scutellar and meristem cells from an immature maize embryo. The methods of the invention comprise administering a transformation-enhancing agent to a plant prior to use of an immature embryo from the plant in a transformation attempt. The methods further comprise transforming a cell from an immature embryo using any method of transformation employing a cell from an immature embryo or a cell descended from an excised immature embryo from a plant. The methods of the invention additionally involve regenerating a transformed embryo or a transformed shoot from a transformed cell. The methods of the present invention do not depend on a particular methods of regenerating embryos or shoots. Any method for regenerating embryos or shoots from a cell known to those of ordinary skill in the art may be employed.

Preferred embodiments involve the transformation-enhancing agent being administered between 0 and 8 days after pollination of the plant. Preferably, the transformation-enhancing agent is administered between 1 and 5 days after pollination of the plant. More preferably, the transformation-enhancing agent is administered between 2 and 4 days after pollination of the plant. The pollinated ear from the maize plant is harvested 1 to 12 days after pollination. Preferably, the pollinated ear from the maize plant is harvested 1 to 10 days after pollination. More preferably, the pollinated ear from the maize plant is harvested 2 to 5 days after pollination.

The transformation-enhancing agents of the invention comprise at least one component. The components are selected from plant growth regulators, alternative carbon sources, plant culture nutrients and compounds and enzymes that alter plant cell wall biosynthesis.

The plant growth regulators of the invention include, but are not limited to, both free and conjugated forms of naturally occurring plant growth regulators. Additionally, the plant growth regulators of the invention encompass synthetic analogues, inhibitors of the synthesis, degradation, transport or action, and precursors of such naturally occurring plant growth regulators. Preferred plant growth regulators include auxins, cytokinins, abscisic acid and ethylene, and conjugates, synthetic analogues, inhibitors and precursors thereof Preferably, auxins would be used at 0.25 mg/L-170 mg/L, more preferably at 1 mg/L-140 mg/L and most preferably at 50 mg/L-100 mg/L.

Naturally occurring and synthetic analogues of auxins include, but are not limited to, indoleacetic acid (IAA), 3-indolebutyric acid (IBA), α-napthaleneacetic acid (NAA), 2,4-dichlorophenoxyacetic acid (2,4-D), 4-(2,4-dichlorophenoxy) butyric acid, 2,4,5-trichlorophenoxyacetic acid (2,4,5-T), (4-chloro-2-methylphenoxy)acetic acid (MCPA), 4-(4-chloro-2-methylphenoxy) butanoic acid (MCPB), mecoprop, dicloprop, quinclorac, picloram, triclopyr, clopyralid, fluroxypyr and dicamba.

Inhibitors of auxins include, but are not limited, inhibitors of enzymes in the biosynthesis pathway leading to the formation of an auxin in a plant and auxin transport inhibitors, such as, for example, 3,4,5-triiodobenzoic acid (TIBA), naphthylphthalamic acid and 9-hydroxyfluorene-9-carboxylic acid. Preferably, auxin transport inhibitors would be used at 1–10 mg/L.

Inhibitors of ABA biosynthesis include, but are not limited to, norflurazon. Preferably, norflurazon would be used at 1–10 mg/L.

Inhibitors of ethylene include, but are not limited to, inhibitors of ethylene synthesis or evolution such as, for example, aminoethoxyvinylglycine (AVG) and silver ions, and inhibitors of ethylene action such as, for example, 2,5-norbornadiene. Preferably, inhibitors of ethylene synthesis would be used at 0.1–0.3 mM.

Naturally occurring and synthetic analogues of cytokinins include, but are not limited to, kinetin, zeatin, zeatin riboside, zeatin riboside phosphate, dihydrozeatin, isopentyl adenine and 6-benzyladenine. Preferably, cytokinins would be used at 0.01 mg/L-2 mg/L.

The transformation-enhancing agents of the invention encompass precursors of plant growth regulators. Such precursors may be used as a substrates for enzymes in the biosynthetic pathways for the synthesis of plant growth regulators in a plant. For example, ethylene precursors may be administered to a plant to increase the level of ethylene in a plant. Ethylene precursors include, methionine, S-adenosylmethionine (SAM), 1-aminocyclopropane-1-carboxylic acid (ACC). In addition, the transformation-enhancing agents of the invention encompass synthetic molecules, such as, for example, ethephon, that can be converted into plant growth regulators by non-enzymatic or enzymatic processes. Preferably, ethylene precursors would be used at 0.2 g/L–0.8 g/L.

Alternative carbon sources of the invention are sources of reduced carbon, other than sucrose, that may be metabolized by a plant. Preferred alternative carbon sources include, but are not limited to, monosaccharides such as, for example, glucose, fructose, galactose, mannose, arabinose, and xylose, disaccharides such as, for example, maltose, lactose and cellobiose, oligosaccaharides such as, for example, raffinose and stachyose, and polysaccharides such as, for example, starch. Also encompassed by the present invention are modified forms of the alternative carbon sources such as, for example, sugar alcohols, carboxylic acids, aldehydes and phosphate esters. Preferably, carbon sources would be used at 30 g/L–80 g/L, more preferably at 2 g/L–100 g/L, and most preferably at 0.2 g/L–150 g/L. Alternatively, carbon sources would be used at 2–30 g/L.

Plant culture nutrients are components found in plant cell and tissue culture media. Such plant cell and tissue culture media are known to those of ordinary skill in the art. A transformation-enhancing agent of the invention may be comprised of one or more components of plant culture media. Preferred, plant culture nutrients include, but are not limited to: standard salt components of plant cell and tissue culture media such as, for example, salts cocktail 3, salts cocktail 4, salts cocktail 2 and salts cocktail 1; nitrate; amino acids; ammonia; phosphate; copper; zinc; and boron. Preferably, nitrate would be used at 0 mg/L–1700 mg/L; preferably, amino acids would be used at 0 mM–50 mM; preferably, ammonia would be used at 100 mg/L–1700 mg/L; preferably, phosphate would be used at 50 mg/L–400 mg /L; preferably, copper would be used at 0 mg/L–0.125 mg/L; preferably, zinc would be used at 0 mg/L–20 mg/L; and preferably, boron would be used at 0 mg/L–10 mg/L.

The transformation-enhancing agents of the invention encompass compounds and enzymes known to alter cell wall biosynthesis in a plant. Any compound or enzyme that can alter cell walls in a plant is encompassed by the present invention. Such compounds and enzymes are known to those of ordinary skill in the art. Enzymes include, but are not limited to those that disturb. cell wall covalent bonds such as, for example, endoglycanases, proteinases and esterases. Compounds that alter cell wall biosynthesis include, but are not limited to, inhibitors of cell wall biosynthesis, compounds that prevent or reduce phenolic crosslinking of cell walls, and compounds that remove calcium from cell walls, compounds that remove proteins and polymers from cell walls by disrupting ionic bonds, compounds that promote acid-induced cell wall expansion and inhibitors of callose formation. Preferably, enzymes would be used at 0.025%–0.75%. Inhibitors of cell wall biosynthesis include, but are not limited to, 2,6-diclorobenzonitrile. Preferably, inhibitors of cell wall biosynthesis would be used at $10^{-7}$–$10^{-4}$ M.

Compounds that prevent or reduce phenolic cross-linking of cell walls include, but are not limited to: anitoxidants that inhibit peroxidases such as, for example, α-tocopherol, ascorbic acid, o-catechol, and N-propyl gallate, iron chelators such as, for example, o-phenanthroline, deferoxamine methanesulfonate, ethylenediamine diacetic acid; calcium ion chelators such as, for example, ethylene glycol-bis-(β-aminoethyl ether)-N,N,N',N'-tetraacetic acid (EGTA), trans-1,2-diamincyclohexanetetraacetic acid (CDTA); copper chelators such as, for example, diethyldithiocarbamate and mercaptobenzothiazole; gibberellins; prolyl hydroxylase inhibitors such as, for example, 3,4-dehydroproline and 3,4-methanoproline; and phenylalanine ammonia lyase inhibitors such as, for example, carboxymethylamine, aminooxyphenylpropanoic acid and p-fluorophenylacetic acid. Preferably, antioxidants would be used at $10^{-7}$–$10^{-2}$ M; preferably, iron chelators would be used at $10^{-7}$–$10^{-4}$ M; preferably, calcium ion chelators would be used at $10^{-7}$–$10^{-2}$ M; preferably, copper chelators would be used at $10^{-7}$–$10^{-2}$ M; preferably, gibberillins would be used at $10^{-7}$–$10^{-4}$ M; preferably, proplyl hydrolase inhibitors would be used at $10^{-7}$–$10^{-2}$ M.

Compounds that remove calcium from cell walls include, but are not limited to, hexammetaphosphate oxalate, EDTA, EGTA and CDTA. Compounds that remove proteins and polymers held in cell walls by ionic bonds include, but are not limited to: high concentrations of salts such as, for example, calcium chloride, potassium chloride, ammonium sulfate, magnesium sulfate, sodium sulfate, calcium phosphate, potassium phosphate and sodium phosphate; thiol-containing reagents such as, for example, as β-mercaptoethanol, dithiothreitol, dithioerythritol; and metal-ion chelators such as, for example, EDTA, EGTA, o-phenanthroline, deferoxamine methanesulfonate, ethylenediamine diacetic acid, diethyldithiocarbamate and mercaptobenzothiazole. Preferably, EDTA, EGTA and CDTA would be used at $10^{-5}$–$10^{-1}$ M; preferably, salts would be used at 0.1M–2.5M; preferably, thiol-containing reagents would be used at $10^{-5}$–$10^{-1}$ M; preferably, metal ion chelators would be used at $10^{-5}$–$10^{-1}$ M.

Other compounds that alter cell walls include those that promote acid-induced cell wall expansion including, but not limited to, auxins and synthetic analogues thereof, low pH buffers, such as, for example, (MES buffer:(2-[N-Morpholino] ethanesulfonic acid, BIS-Tris buffer: (bis [2Hydroxyethyl] iminotris[hydroxymethyl]methane; 2-bis [2Hydroxyethylamino-2-[hydroxymethyl]-1,3-propanediol)), fusicoccin and α-napthylacetate. The transformation-enhancing agents also include compounds that inhibit callose formation including, but not limited, EGTA, difluoromethylornithine (DFMO), α-difluoromethylarginine, 4-methylmorpholine-N-oxide and dimethylsulfoxide. Preferably, low pH buffers would be used at 0.2–1 g/L, preferably, fusicoccin and napthylacetate would be used at $10^{-5}$–$10^{-1}$ M; preferably, compounds that inhibit callose formation would be used at 0.05–0.1%.

Transformation-enhancing agents in the following amounts can be utilized in this invention:

TABLE 1

| Transformation-enhancing agents | Component | Range 1 | Range 2 | Range 3 | Unit |
|---|---|---|---|---|---|
| dicamba | dicamba | 80–120 | 60–140 | 30–170 | μM |
| hormone cocktail* | dicamba | 80–120 | 60–140 | 30–170 | mg/L |
| | 2,4-D | 1.5–2.5 | 1–3 | 0.5–3.5 | mg/L |
| | boric acid | 2.8–4.0 | 2–4.8 | 1.4–5.4 | g/L |
| | L-proline | 160–240 | 140–260 | 120–280 | mg/L |
| | MES buffer | 0.40–0.6 | 0.25–0.75 | 0.1–0.9 | g/L |
| 2,4-D | 2,4-D | 300–700 | 200–800 | 100–900 | mg/L |
| liquid callus medium† | sucrose | 48.5–88.5 | 38.5–98.5 | 28.5–108.5 | g/L |
| | glucose | 24–28 | 18–54 | 12–60 | g/L |
| ABA | ABA | 0.3–0.7 | 0.2–0.8 | 0.1–0.9 | μM |
| Pluronic F68 | Pluronic F68 | 400–600 | 300–700 | 200–800 | mg/L |
| proline mix | thioproline | 0.3–0.5 | 0.2–0.6 | 0.1–0.7 | mM |
| | L-proline | 20–30 | 15–35 | 10–40 | mM |
| | potassium chloride | 40–60 | 35–65 | 25–75 | mM |
| | EGTA | 0.75–1.25 | 0.65–1.35 | 0.5–1.5 | mM |
| ACC | ACC | 0.4–0.6 | 0.3–0.7 | 0.25–0.75 | mM |
| AVG | AVG | 0.18–0.22 | 0.16–0.24 | 0.15–0.25 | mM |
| salts cocktail 4 | potassium nitrate | 1.4–1.8 | 1.2–2.0 | 1.0–2.6 | g/L |
| formulation | ammonium sulfate | 1.5–1.9 | 1.0–2.4 | 0.5–2.9 | g/L |
| | boric acid | 2–4 | 1.5–4.5 | 0.5–5.5 | mg/L |
| salts cocktail 2 | potassium nitrate | 2.0–3.0 | 1.75–3.25 | 1.5–3.5 | g/L |
| formulation | ammonium sulfate | 0.08–0.19 | 0.05–0.22 | 0.04–0.23 | g/L |
| | boric acid | 2–4 | 1.5–4.5 | 0.5–5.5 | mg/L |
| salts cocktail 1 | potassium nitrate | 1.7–2.1 | 1.5–2.3 | 1.2–2.6 | g/L |
| formulation | ammonium nitrate | 1.5–1.9 | 1.0–2.4 | 0.5–2.9 | g/L |
| | boric acid | 4.2–8.2 | 4.2–8.4 | 3.2–9.2 | mg/L |
| salts cocktail 3 | potassium nitrate | 2.53–3.13 | 2.33–3.23 | 2.03–3.63 | g/L |
| | ammonium sulfate | 0.36–0.56 | 0.26–0.66 | 0.16–0.76 | g/L |
| | boric acid | 1.4–1.8 | 1.2–2.0 | 1.0–2.6 | mg/L |

*pH 4.0
†See components of 604 medium in Table 13. (Gelrite was omitted and non standard levels of sucrose and glucose were used).

In the present invention, a transformation-enhancing agent can be formulated with an acceptable carrier into a transformation-enhancing composition that is for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, an encapsulating agent, a binder, an emulsifier, a dye, a U.V. protectant, a buffer, a flow agent or fertilizers, micronutrient donors or other preparations that influence plant growth. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. The active ingredients of the present invention are normally applied in the form of compositions and can be applied to the crop area or plant to be treated, simultaneously or in succession, with other compounds. Preferred methods of applying a transformation-enhancing agent of the present invention or a transformation-enhancing composition of the present invention are ear infusion, ear injection, application to the ear in a lanolin paste (Dietrich et al. (1995) *Plant Physiol. Biochem.* 33:327–336; Lur and Setter (1993) *Annals of*

*Botany* 72:1–6), shank injection, stem injection, application with an I.V. (Boyle et al. (1991) *Crop Sci.* 31:1241–1245; Zhou and Smith (1996) Crop Sci. 36:452–456) and foliar application. The number of applications and the rate of application depend on the species of plant, genotype of plant and the desired outcome.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g. butyl-naphthalene sulfonate; salts of sulfonated naphthalene-formaldehyde condensates; salts of sulfonated phenol-formaldehyde condensates; more complex sulfonates such as the amide sulfonates, e.g. the sulfonated condensation product of oleic acid and N-methyl taurine; or the dialkyl sulfosuccinates, e.g. the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitar fatty acid esters, block copolymers of ethylene oxide and propylene oxide, acetylenic glycols such as 2,4,7,9-tetraethyl-5-decyn4,7-diol, or ethoxylated acetylenic glycols. Examples of a cationic surface-active agent include, for instance, an aliphatic mono-, di, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates or botanical materials such as cork, powdered corncobs, peanut hulls, rice hulls, and walnut shells.

The compositions of the present invention can be in a suitable form for direct application or as concentrate of primary composition which requires dilution with a suitable quantity of water or other diluent before application. The transformation-enhancing agent concentration will vary depending upon the nature of the particular formulation, specifically, whether it is a concentrate or to be used directly. The compositions of the present invention will be administered to the plants of interest at a rate per plant or per acre which provides the plants with an effective amount of the transformation-enhancing agent. Such a rate depends on the concentration of the transformation-enhancing agent in the composition and the dilution, if any, of the composition.

The transformation-enhancing agents and compositions can be administered to a plant by, for example, injecting, infusing, pipeting, spraying, atomizing, dusting, scattering, coating or pouring, introducing into or on the soil, introducing into irrigation water, by seed treatment or general application or dusting at the time prior to the introduction of the DNA construct or DNA construct-carrying bacteria to the plant tissue to be transformed.

The methods of the present invention involve genetically transforming plants. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Bowen et al. U.S. Pat. No. 5,736,369 (cereals); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), sunflower (*Helianthus annuus*), safflower (*Carthamus tinctorius*), millet (*Pennisetum glaucum, Panicum miliaceum, Eleusine coracana, Setaria italica*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integnfolia*), almond (*Prunus amygdalus*), sugar beets (*Beta vulgaris*), oats, barley (*Hordeum vulgare*), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock. (*Tsuga canadensis*); Sitka spruce (*Picea glauca*); redwood (*Sequoia sempervirens*); true firs such as silver fir (*Abies amabilis*). and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, safflower, canola, soybean, cotton, peanut, sorghum, rice, wheat, millet, tobacco, etc), more preferably corn and soybean plants, yet more preferably corn plants.

Experimental

EXAMPLE I

Pre-harvest Ear Treatments and Maize Transformation

Current maize transformation systems, designed for fast-growing and highly embryogenic cultures, produce high frequencies of transgenic events in genetic lines such as, for example, GS3 and certain model maize inbreds. Generally, elite inbreds of maize display relatively low frequencies of transformation and regeneration of transformed plants. While the cause of such low frequencies of transformation and regeneration may be due to any one or more of a multitude of causes, the most likely cause may be the poor embryogenic response of callus cells derived from elite inbreds. Thus, increasing the embryogenic response of cells of such elite inbreds may increase transformation efficiencies with these elite genetic lines. Maize elite inbreds P38 and N46 are members of two distinct heterotic groups and prove difficult to culture and transform.

To attempt to increase transformation efficiency, a variety of agents were infused separately into immature maize ears prior to harvest of the immature embryos for a transformation attempt. Of particular interest were compounds that may increase the embryogenic response of maize callus.

Ears from greenhouse-grown or field-grown maize elite inbreds, P38 and N46, were treated with one of the following agents or combinations of agents at three days after pollination: dicamba, hormone cocktail, 2,4-D (2,4-dichlorophenoxyacetic acid), callus medium, water, ABA, Pluronic F68, proline mix, ACC, AVG, salts cocktail 4, salts cocktail 2 (Gamborg et al. (1968) *Exp. Cell Res.* 50:151), salts cocktail 1 (Murashige and Skoog (1962) *Physiol. Plant.* 15:473), salts cocktail 3 (Chu et al. (1975) *Scientia Sinic.* 18:659), 2,4D+salts cocktail 1, 2,4-D+salts cocktail 3, 2,4-D+dicamba and dicamba+ACC. The transformation-enhancing agents and combinations were prepared in water at the concentrations indicated in Table 1. The combinations contained each component agent at the concentrations indicated in Table 1. The solutions were filter sterilized before applying to the ears at a rate of 10 mL/ear. The solutions were applied to the ears by injecting between the silks and husks at three days post pollination. Care was taken not to disrupt the ears.

The transformation-enhancing agents were also administered with an I.V. The I.V. was typically placed into the stalk just below the node subtending the developing ear. A cork borer was used to create a hole in the stalk which was filled with sterile water after which the site was wrapped with rubber electrician's tape. A 50 mL syringe connected to a butterfly I.V. was taped above the infusion site and the needle was inserted through the tape and into the hole. Once set up, the I.V. was started by removal of a clamp in the tubing. Target sites would be the both the xylem and phloem: the xylem for transport of water and dissolved substances upward in the plant body, and the phloem for transport of organic materials such as sugars and amino acids both upwards and downwards and for delivery to sink sources. Transport was evaluated through the use of food dyes where both upward and downward movement was observed.

TABLE 2

Concentrations of Transformation-Enhancing Agents

| Transformation-enhancing agents | Component | Concentration | Unit |
|---|---|---|---|
| dicamba | dicamba | 100 | µM |
| hormone cocktail* | dicamba | 100 | mg/L |
|  | 2,4-D | 2 | mg/L |
|  | boric acid | 3.4 | g/L |
|  | L-proline | 200 | mg/L |
|  | MES buffer | 0.5 | g/L |
| 2,4-D | 2,4-D | 500 | mg/L |
| liquid callus medium† | sucrose | 68.5 | g/L |
|  | glucose | 36 | g/L |
| ABA | ABA | 0.5 | µM |
| Pluronic F68 | Pluronic F68 | 500 | mg/L |
| proline mix | thioproline | 0.4 | mM |
|  | L-proline | 25 | mM |
|  | potassium chloride | 50 | mM |
|  | EGTA | 0.1 | mM |
| ACC | ACC | 0.5 | mM |
| AVG | AVG | 0.2 | mM |
| salts cocktail 4 formulation | potassium nitrate | 1.6 | g/L |
|  | ammonium sulfate | 1.7 | g/L |
|  | boric acid | 3 | mg/L |
| salts cocktail 2 formulation | potassium nitrate | 2.5 | g/L |
|  | ammonium sulfate | 0.134 | g/L |
|  | boric acid | 3 | mg/L |
| salts cocktail 1 formulation | potassium nitrate | 1.9 | g/L |
|  | ammonium nitrate | 1.65 | g/L |
|  | boric acid | 6.2 | mg/L |
| salts cocktail 3 formulation | potassium nitrate | 2.83 | g/L |
|  | ammonium sulfate | 0.46 | g/L |
|  | boric acid | 1.6 | mg/L |

*pH 4.0
†See components of 604 medium in Table 13. (Gelrite was omitted and non standard levels of sucrose and glucose were used).

Transformation-enhancing compounds were also introduced via lanolin. kLanolin paste was typically applied at a mass of 1 gram per ear. Husks were peeled back, but not removed, silks were removed, and the lanolin mixed with the compound was applied to the pericarp of the developing seed using a spatula. Ears were divided into halves longitudinally: one half would received lanolin with the compound and the other half received only lanolin.

For transformation by particle bombardment, maize ears were harvested at ten days after pollination and surface sterilized in 50% CHLOROX™ laundry bleach plus 0.5% Tween 20 surfactant for 20 minutes, and rinsed two times with sterile water. The immature embryos were excised and placed embryo axis side down (scutellum side up), 25 embryos per plate, on 604 medium, incubated at 28° C. in the dark for three days. Prior to bombardment, all embryos were transferred to plates containing 604 medium and 15% sucrose and then aligned within the 2.5-cm target zone in preparation for bombardment. Al media recipes are in the Table 10–18.

A plasmid vector comprising the coding region of uidA operably linked to a ubiquitin promoter was made. This plasmid DNA plus plasmid DNA containing a BAR selectable marker gene operably linked to the double 35S promoter was precipitated onto 1.1 μm (average diameter) tungsten pellets using a $CaCl_2$ precipitation procedure as follows:

100 μL prepared tungsten particles in water

10 μL (0.1 μg/μl) DNA in Tris-EDTA buffer (1 μg total)

100 μL 2.5 M $CaCl_2$

20 μL 0.1 M spermidine

The final mixture was sonicated briefly and allowed to incubate under constant vortexing for 10 minutes. After the precipitation period, the tubes were centrifuged briefly, liquid removed, washed with 500 mL 100% ethanol, and centrifuged for 30 seconds. Again the liquid was removed, and 60 μL 100% ethanol was added to the final tungsten particle pellet. For particle gun bombardment, the tungsten/DNA particles were briefly sonicated and 10 μL spotted onto the center of each macrocarrier and allowed to dry about two minutes before bombardment.

The sample plates were bombarded at level #4 in a Biorad PDS-1000 Helium gun. All samples received a single shot at 650 PSI, with a total of six aliquots taken from each tube of prepared particles/DNA. Following bombardment the embryos were maintained on 604 medium +15% sucrose for three days in the dark, and then transferred to 604S medium with 3 mg/L bialaphos, maintained for three weeks on 3 mg/L bialaphos, and then transferred to 604J at 5 mg/L bialaphos. Once herbicide-resistant colonies were well established and ready for regeneration, approximately eight weeks after bombardment, the herbicide-resistant colonies were transferred to 288O regeneration medium containing 3 mg/L bialaphos, maintained in the dark or seven days, and then transferred to the light at 28° C. for shoot formation and elongation. Callus response, colony and plant recovery and GUS gene expression were monitored during the course of the experiments.

Agrobacterium-mediated transformation of maize was also employed. See, U.S. application Ser. No. 08/788,018, herein incorporated by reference.

EXAMPLE II

Effects of Pre-harvest Dicamba Treatments on Maize Transformation

The effects of injecting into ears three days after pollination 10 mL of a 100 μM of dicamba, an auxin analogue, on maize transformation was investigated. Ears were injected with 10 mL of a 100 μM solution of dicamba three days post pollination The ear injection was conducted as described in Example I. Based on this experiment with elite inbred P38, the Type I embryogenic callus response rate in the embryos from ears pre-treated with 100 μM dicamba was higher early in the experiment, and was maintained over the course of the study (Table 2). The standard, non pre-treated control gave a high early callus response rate and then showed a consistent decline, typical for the genotype. Plant recovery was low based on the number of colonies with healthy phenotypes at the time of transfer to regeneration. Of the plants which were recovered, three colonies produced escapes: two from the dicamba pre-treatment and one from the control. The plants recovered that are transgenic, based on GUS histochemical assays and herbicide-resistance (on the basis of 1% Ignite leaf painting assay) have normal phenotypes and do not appear to have any fertility problems.

TABLE 3

Effects of a Pre-harvest Dicamba Treatment

| Ear Pre-Treatment | 21 Day Callus Response | 42 Day Callus Response | 56 Day Callus Response | Colonies Expressing GUS | Colonies to Regeneration | Colonies to Plants | Plants Transformed* |
|---|---|---|---|---|---|---|---|
| 100 μM dicamba | 37.9% (146/385) | 40% (154/385) | 32.2% (124/385) | 8.6% (33/385) | 29.1% (112/385) | 4.2% (14/385) | 3.11% (12/385) |
| standard | 26.4% (46/174) | 22.9% (41/179) | 17.2% (30/174) | 4% (7/174) | 14.4% (25/174) | 1.7% (3/174) | 1.2% (2/174) |

*Transformation by particle bombardment.

In a similar experiment, three callus media were tested to determine if any one was significantly better than the others in producing embryogenic callus following a pretreatment with 100 μM dicamba (Table 3). Prior to bombardment, freshly excised embryos were placed onto either 560P, 601H, or 604 medium and incubated at 28° C. in the dark for three days. Prior to bombardment, all embryos were transferred to 604 with 15% sucrose. On observation at 42 days after callus initiation, 604 and 560P gave equal levels of colony recovery whereas tissue on 601H initiated callus, but showed a lack of growth and a quick death on selection. Colonies were transferred to regeneration medium containing 3 mg/L Bialaphos after 8–9 weeks in culture. No embryogenic colonies were observed for the controls during the course of the experiment. Only one colony was capable of regeneration from this experiment and that colony was from the 100 μM dicamba/560P treatment.

TABLE 4

Effects of Pre-bombardment Medium on the Dicamba Response

| Ear Pre-Treatment | Number of Embryos | Initial Culture Medium | 21 Day Callus Response | 42 Day Callus Response | Colonies with GUS Expression | Colonies to Regeneration | Colonies to Plants* |
|---|---|---|---|---|---|---|---|
| 100 μM dicamba | 84 | 601H | 17.9%(16) | 16.5%(14) | 2.4%(2) | 4.8%(4) | 0% |
| 100 μM dicamba | 79 | 560P | 12.7%(10) | 24%(19) | 2.5%(2) | 2.5%(2) | 1.3%(1) |
| 100 μM dicamba | 128 | 604 | 23.4%(30) | 33%(42) | 4.7%(6) | 11.7%(15) | 0% |
| none (control) | 96 | 601H | 2.1%(2) | 11.5%(11) | 2.1%(2) | 0% | 0% |
| none (control) | 99 | 560P | 19.2%(19) | 20.2%(20) | 0% | 0% | 0% |
| none (control) | 108 | 604 | 11.1%(12) | 21.3%(23) | 0.92%(1) | 0% | 0% |

*Transformation by particle bombardment.

EXAMPLE III

Effects of Pre-harvest Synthetic Auxin Treatments

Given the transformation enhancement caused by a dicamba pre-harvest ear treatment, a variety of other agents were tested for the ability to enhance transformation processes when applied in a similar manner as dicamba to ears at three days after pollination. The ear injection was conducted as described in Example I. Other synthetic auxins were tested for their effects on the transformation of N46 and P38 maize. The results with synthetic auxins and a no pre-treatment control are summarized in Table 4. With N46 maize, significant increase in the percent of transformed colonies over the control were observed for all synthetic auxin treatments tested. Clearly, the superior transformation results with N46 maize were obtained with the hormone cocktail and dicamba treatments. With P38 the results were more variable. Only the homone cocktail and 2,4-D treatments had significantly greater percentages of transformed colonies than the control.

EXAMPLE IV

Effects of Pre-harvest Plant Growth Regulator Treatments

An endogenous plant growth regulator, abscisic acid (ABA), and other compounds known to influence plant growth were tested for their effects on maize transformation when applied to ears at four days after pollination using the injection method described in Example I. Additionally, the effect of the injection of water was also tested. With inbred genetic line N46, the largest increase in percent colony transformation above the control was with the ABA treatment (Table 5). A significant increase in the percentage of transformed colonies, relative to the control, for N46 was also detected with proline mix. Interestingly, similar increases in the percentage of transformed colonies, relative to the control, for N46 were also detected with treatments containing aminocyclopropane-1-carboxylic acid (ACC) and (2-aminoethoxyvinyl)glycine (AVG). ACC is a product

TABLE 5

Effects of Pre-harvest Synthetic Auxin Treatments on Maize Transformation

| Infusate | Inbred Line | Number of Ears | Number of Embryos | Number of GUS Positive Colonies | Percent Colony Transformation* |
|---|---|---|---|---|---|
| hormone cocktail | N46 | 6 | 276 | 25 | 9.10% |
|  | P38 | 9 | 212 | 8 | 3.80% |
| dicamba | N46 | 12 | 936 | 89 | 9.50% |
|  | P38 | 13 | 1061 | 11 | 1.10% |
| 2,4-D | N46 | 3 | 147 | 4 | 2.70% |
|  | P38 | 1 | 48 | 2 | 4.20% |
| callus medium 24 hrs.† | N46 | 3 | 64 | 4 | 6.30% |
|  | P38 | 4 | 62 | 0 | 0% |
| control(no infusion) | N46 | 10 | 567 | 22 | 3.80% |
|  | P38 | 25 | 1220 | 11 | 0.90% |

*Agrobacterium-mediated transformation.
†Callus medium was applied 24 hrs. before ears were harvested for transformation.

of the reaction catalyzed by ACC synthase and a substrate of the reaction catalyzed by ACC oxidase, the ethylene-forming enzyme. AVG, on the other hand, is an inhibitor of ACC synthase. With inbred genetic line P38, only the AVG and water treatments increased the percentage of transformed colonies above the level of the control.

TABLE 6

Effects of Pre-harvest Plant Growth Regulator Treatments on Maize Transformation

| Infusate | Inbred Line | Number of Ears | Number of Embryos | Number of GUS Positive Colonies | Percent Colony Transformation* |
|---|---|---|---|---|---|
| ABA | N46 | 2 | 124 | 25 | 20% |
|  | P38 | 5 | 257 | 0 | 0% |
| Pluronic F68 | N46 | 6 | 422 | 10 | 2.40% |
| proline mix | N46 | 4 | 110 | 10 | 9.10% |
| water | N46 | 13 | 656 | 27 | 4.20% |
|  | P38 | 16 | 863 | 16 | 2% |
| ACC | N46 | 3 | 176 | 12 | 6.80% |
|  | P38 | 1 | 53 | 0 | 0% |
| AVG | N46 | 2 | 48 | 3 | 6.30% |
|  | P38 | 3 | 113 | 2 | 1.80% |
| control (no infusion) | N46 | 10 | 567 | 22 | 3.80% |
|  | P38 | 25 | 1220 | 11 | 0.90% |

*Agrobacterium-mediated transformation.

EXAMPLE V

Effects of Pre-harvest Nitrogen/Ammonia Treatments

Several nitrogen-containing treatments were applied to ears at three days after pollination. The treatments employed are salt formulations that are commonly used in plant tissue culture media including salts cocktail 4, salts cocktail 2, salts cocktail 1 and salts cocktail 3. The salt formulations were applied by injection to ears as described in Example I. Of these treatments, only the salts cocktail 1 provided an increased percentage of colony transformation over the control (Table 6). The salts cocktail 1 treatment provided an enhancement for both N46 and P38 maize transformation.

TABLE 7

Effects of Pre-harvest Nitrogen/Ammonia Treatments on Maize Transformation

| Infusate | Inbred Line | Number of Ears | Number of Embryos | Number of GUS Positive Colonies | Percent Colony Transformation* |
|---|---|---|---|---|---|
| salts cocktail 4 | N46 | 1 | 66 | 1 | 1.50% |
| salts cocktail 2 | N46 | 1 | 74 | 0 | 0% |
|  | P38 | 2 | 263 | 0 | 0% |
| salts cocktail 1 | N46 | 1 | 94 | 5 | 5.30% |
|  | P38 | 2 | 99 | 4 | 4% |
| salts cocktail 3 | N46 | 2 | 29 | 1 | 3.40% |
| control (no infusion) | N46 | 10 | 567 | 22 | 3.80% |
|  | P38 | 25 | 1220 | 11 | 0.90% |

*Agrobacterium-mediated transformation.

EXAMPLE VI

Effects of Pre-harvest Combination Treatments

Finally, some combination treatments were examined for their effects on the transformation of N46 and P38 maize (Table 7). The combinations were applied by ear injection as described in Example I. None of the combinations provided significant increase in transformation efficiency with N46 maize. However, the 2,4-D+salts cocktail 1 formulation and 2,4-D+salts cocktail 3 formulation treatments each increased the percentage of colony transformation with P38 maize. Thus, some of the combination treatments provide a useful enhancement of the transformation of P38 maize.

agents were applied to separate ears at three days after pollination in a lanolin paste. The method employed for applying the transformation-enhancing agents of the invention to ears in lanolin paste is described in Example I. Ears were divided into halves longitudinally with one half of the ear receiving lanolin with zeatin riboside or 2,4-D and the other half receiving only lanolin. An additional ear that was not treated was used as a control.

The results are presented in Table 8. Regenerable colonies and transformed maize plants were recovered from both the zeatin riboside and 2,4-D treatments, but not with either of

TABLE 8

Effects of Pre-harvest Combination Treatments on Maize Transformation

| Infusate | Inbred Line | Number of Ears | Number of Embryos | Number of GUS Positive Colonies | Percent Colony Transformation* |
|---|---|---|---|---|---|
| 2,4-D + salts cocktail 1 formulation | N46 | 1 | 76 | 3 | 3.90% |
| | P38 | 1 | 28 | 2 | 7.10% |
| 2,4-D + salts Cocktail 3 formulation | P38 | 1 | 24 | 1 | 4.20% |
| 2,4-D + dicamba | N46 | 2 | 126 | 1 | 0.80% |
| dicamba + ACC | N46 | 1 | 42 | 0 | 0% |
| | P38 | 2 | 89 | 1 | 1.10% |
| control (no infusion) | N46 | 10 | 567 | 22 | 3.80% |
| | P38 | 25 | 1220 | 11 | 0.90% |

*Agrobacterium-mediated transformation.

EXAMPLE VII

Effects of Lanolin-Paste Applications of Zeatin Riboside and 2,4-D

The effects of pre-harvest ear treatments of zeatin riboside and 2,4-D on maize transformation were investigated. Both the lanolin controls or the non-treated control. The results indicate that administering either zeatin riboside or 2,4-D to ears in a lanolin paste before harvest for a transformation attempt increase both the percentages of regenerable colonies and transformed plants relative to untreated ears and lanolin-treated ears.

TABLE 9

Effects of Lanolin-Paste Applications of Zeatin Riboside and 2,4-D

| Transformation-Enhancing Agent | 21 Day Callus Response | 42 Day Callus Response | Regenerable Colonies | Plants Transformed* |
|---|---|---|---|---|
| 0.5% Zeatin riboside in Lanolin (Ear 1) | 9.4% | 9.4% | 0.6% | 0.6% |
| Lanolin control (Ear 1) | 4.2% | 5.9% | 0% | 0% |
| 0.5% 2,4-D in Lanolin (Ear 2) | 15.4% | 12.5% | 1.5% | 1.5% |
| Lanolin control (Ear 2) | 16.4% | 11.2% | 0% | 0% |
| Non-treated control (Ear 3) | 58% | 24% | 0% | 0% |

*Transformation by particle bombardment.

EXAMPLE VIII

Effects of Intervenous Applications of Liquid Callus Initiation Medium

The effect on maize transformation of I.V. delivery of liquid callus initiation medium (Medium 604), with controls of water and no infusion, on pre-harvest ears was evaluated using particle mediated DNA delivery. Solutions were prepared and administered through I.V. set-ups as described in Example 1, with 50 ml volume of delivery beginning at four days after pollination. The results are presented in Table 9. Regenerable colonies were recovered only from the ears infused with liquid callus initiation medium, with only one colony capable of producing plants able to survive in the greenhouse environment. These data indicate that the administration of liquid callus medium into an immature ear before harvest for transformation can provide a benefit in the recovery of both transgenic and regenerable colonies as compared to the untreated ears.

Data for I.V. injections are included below:

TABLE 10

Genotype N46

| Infusion I.V. Treatment | Percent Type I Colony Recovery | Percent GUS positive Colonies | Percent Transgenic Plant Recovery |
|---|---|---|---|
| Modified 604 | 29.3% (77/263) | 0.76% (2/263) | 0.38% (1/263) |
| Water | 11.4% (14/123) | 0% | 0% |
| No Infusion | 12.5% (9/72) | 0% | 0% |

*Percentages were calculated based on the number of embryos involved in the original transformation
*Modified 604 medium was altered from the original recipe to contain 68.5 g/L sucrose and 36 g/L glucose A variety of agents were identified that increase the percentage of colonies transformed when injected into maize ears three days after pollination and about a week before harvest for use in a transformation attempt. Two elite inbred genetic lines of maize, N46 and P38, were utilized in the investigations. An interaction between the ear treatment and the elite inbred line was observed for the percentage of colonies transformed. Thus, for a particular genetic line of maize, a variety of agents should be tested in a manner similar to that described herein to determine the best ear treatment for enhancing transformation.

Several treatments provided increased percentages of colonies transformed for both genetic lines. These treatments include the hormone cocktail, AVG and the salts cocktail 1 formulation. Further enhancement of transformation may be achieved by applying two of more of these agents to an ear prior to harvest for a transformation attempt. The two or more agents may be applied at the same time or sequentially to provide additional enhancements in transformation.

TABLE 11

560P Medium

| Components | Amount | | mg/L |
|---|---|---|---|
| D-I water | 950 ml | | |
| N6 salts | 4 g | | |
| | | ammonium sulfate | 436 |
| | | boric acid | 1.6 |
| | | calcium chloride anhydrous | 332.2 |
| | | Na2.EDTA | 37.25 |
| | | ferrous sulfate-7H2O | 27.85 |
| | | magnesium sulfate | 90.37 |
| | | manganese sulfate | 3.33 |
| | | potassium iodide | 0.8 |
| | | potassium nitrate | 2830 |
| | | potassium phosphate monobasic | 400 |
| | | zinc sulfate-7H2O | 1.5 |
| Eriksson's vitamin mix (1000X) | 1 ml | | |
| | | Glycine | 2 |
| | | Nicotinic acid | 0.5 |
| | | Pyridoxine | 0.5 |
| | | Thiamine.HCl | 0.5 |
| Thiamine-HCl | 0.5 mg | | |
| Sucrose | 30 g | | |
| 2,4-D | 2.0 mg | | |
| L-Proline | 0.690 g | | |
| Gelrite | 3 g | | |
| silver nitrate | 0.85 mg | | |

TABLE 12

| Components | Amount | | mg/L |
|---|---|---|---|
| D-I water | 900 ml | | |
| MS salts | 4.3 g | | |
| | | ammonium nitrate | 1650 |
| | | boric acid | 6.2 |
| | | Calcium chloride anhydrous | 332.2 |
| | | Colbalt chloride 6H2O | 0.025 |
| | | Cupric sulfate 5H2O | 0.025 |
| | | Na2-EDTA | 37.26 |
| | | Ferrous sulfate-7H2O | 27.8 |
| | | magnesium sulfate | 180.7 |
| | | manganese sulfate | 16.9 |
| | | Molybdic acid (Na salt) | 0.25 |
| | | potassium iodide | 0.83 |
| | | potassium nitrate | 1900 |
| | | Potassium phosphate monobasic | 170 |
| | | zinc sulfate-7H2O | 8.6 |
| myo-inositol | 0.1 g | | |
| MS vitamins | 5 ml | | |
| | | glycine | 2 |
| | | myo-Inositol | 100 |
| | | Nicotinic acid | 0.5 |
| | | Pyridoxine.HCl | 0.5 |
| | | Thiamine.HCl | 0.1 |
| S&H vitamins | 10 ml | | |
| | | myo-Inositol | 1000 |
| | | nicotinic acid | 5 |
| | | pyridoxine.HCl | 0.5 |
| | | thiamine.HCl | 5 |
| potassium nitrate | 5.6 g | | |
| casein hydrolysate acid | 0.5 g | | |
| L-proline | 2.76 g | | |
| Glucose | 10 g | | |
| Surcose | 20 g | | |
| 2,4-D | 2 mg | | |
| Gelrite | 2.4 g | | |
| silver nitrate | 8.5 mg | | |
| Zeatin | 0.1 mg | | |

TABLE 13

| Components | Amount | mg/L |
|---|---|---|
| D-I water | 900 ml | |
| N6 salts | 1.6 g | |
| ammonium sulfate | | 436 |
| Boric acid | | 1.6 |
| calcium chloride anhydrous | | 332.2 |
| Na2-EDTA | | 37.25 |
| ferrous sulfate-7H2O | | 27.85 |
| magnesium sulfate | | 90.37 |
| manganese sulfate | | 3.33 |
| potassium iodide | | 0.8 |
| potassium nitrate | | 2830 |
| potassium phosphate monobasic | | 400 |
| zinc sulfate-7H2O | | 1.5 |
| N6 macronutrients (10X) | 60 ml | |
| Potassium nitrate | 1.680 g | |
| B5H minor salts (1000X) | 0.6 ml | |
| B5H Fe Na EDTA (100x) | 6 ml | |
| Eriksson's vitamin mix (1000X) | 0.4 ml | |
| S&H vitamins (100X) | 6 ml | |
| Glycine | | 2 |
| Nicotinic acid | | 0.5 |
| Pyridoxine | | 0.5 |
| Thiamine.HCl | | 0.5 |
| myo-Inositol | | 1000 |
| nicotinic acid | | 5 |
| pyridoxine.HCl | | 0.5 |
| thiamine.HCl | | 5 |
| thiamine.HCl | 0.2 mg | |
| L-Proline | 1.98 g | |
| casein hydrolysate acid | 0.3 g | |
| Glucose | 0.6 g | |
| Sucrose | 20 g | |
| 2,4-D | 0.8 mg | |
| Gelrite | 2 g | |
| Dicamba | 1.2 mg | |
| silver nitrate | 3.4 mg | |

TABLE 14

| Components | Amount | mg/L |
|---|---|---|
| D-I water | 900 ml | |
| N6 salts | 1.6 g | |
| ammonium sulfate | | 436 |
| boric acid | | 1.6 |
| calcium chloride anhydrous | | 332.2 |
| Na2-EDTA | | 37.25 |
| ferrous sulfate-7H2O | | 27.85 |
| magnesium sulfate | | 90.37 |
| manganese sulfate | | 3.33 |
| potassium iodide | | 0.8 |
| potassium nitrate | | 2830 |
| Potassium phosphate monobasic | | 400 |
| zinc syulfate-7H2O | | 1.5 |
| N6 macronutrients (10X) | 60 ml | |
| potassium nitrate | 1.680 g | |
| B5H minor slats (1000X) | 0.6 ml | |
| B5H Fe Na EDTA (100x) | 6 ml | |
| Eriksson's vitamin mix (1000X) | 0.4 ml | |
| S & H vitamins (100X) | 6 ml | |
| glycine | | 2 |
| nicotinic acid | | 0.5 |
| pyridoxine | | 0.5 |
| Thiamine.HCl | | 0.5 |
| myo-Inositol | | 1000 |
| nicotinic acid | | 5 |
| pyridoxine.HCl | | 0.5 |
| thiamine.HCl | | 5 |
| thiamine.HCl | 0.2 mg | |
| L-Proline | 1.98 g | |
| casein hydrolysate acid | 0.3 g | |
| glucose | 0.6 g | |
| sucrose | 120 g | |
| 2,4-D | 0.8 mg | |
| gelrite | 2 g | |
| dicamba | 1.2 mg | |
| silver nitrate | 3.4 mg | |

TABLE 15

| Components | Amount | | mg/L |
|---|---|---|---|
| D-I water | 900 ml | | |
| N6 salts | 1.6 g | | |
| | | ammonium sulfate | 436 |
| | | boric acid | 1.6 |
| | | calcium chloride anhydrous | 332.2 |
| | | Na2-EDTA | 37.25 |
| | | ferrous sulfate-7H2O | 27.85 |
| | | magnesium sulfate | 90.37 |
| | | magnanese sulfate | 3.33 |
| | | potassium iodide | 0.8 |
| | | potassium nitrate | 2830 |
| | | Potassium phosphate monobasic | 400 |
| | | zinc syulfate-7H2O | 1.5 |
| N6 macronutrients (10X) | 60 ml | | |
| potassium nitrate | 1.680 g | | |
| B5H minor slats (1000X) | 0.6 ml | | |
| B5H Fe Na EDTA (100x) | 6 ml | | |
| Eriksson's vitamin mix (1000X) | 0.4 ml | | |
| | | glycine | 2 |
| | | nicotinic acid | 0.5 |
| | | pyridoxine | 0.5 |
| | | Thiamine.HCl | 0.5 |
| S & H vitamins (100X) | 6 ml | | |
| | | myo-Inositol | 1000 |
| | | nicotinic acid | 5 |
| | | pyridoxine.HCl | 0.5 |
| | | thiamine.HCl | 5 |
| thiamine.HCl | 0.2 mg | | |
| L-Proline | 1.98 g | | |
| casein hydrolysate acid | 0.3 g | | |
| glucose | 0.6 g | | |
| sucrose | 120 g | | |
| 2,4-D | 0.8 mg | | |
| gelrite | 2 g | | |
| dicamba | 1.2 mg | | |
| silver nitrate | 3.4 mg | | |

TABLE 16

| Components | Amount |
|---|---|
| D-I water | 950 ml |
| boric acid | 3 g |
| manganous sulfate monohydrate | 10 g |
| zinc sulfate 7H2O | 2 g |
| sodium molybdate dihydrate | 0.25 g |
| cupric sulfate 5H2O | 0.025 g |
| potassium iodide | 0.75 g |
| cobalt chloride 6H2O | 0.025 g |

TABLE 17

| Components | Amount |
|---|---|
| D-I water | 950 ml |
| calcium chloride dihydrate | 1.66 g |
| Ammonium sulfate | 4.620 g |
| Potassium phosphate monobasic | 4.00 g |
| manganese sulfate 7-H2O | 1.850 g |
| Potassium nitrate | 28.300 g |
| B5H Fe Na EDTA(100x) | |
| D-I water | 950 ml |
| disodium EDTA dihydrate | 3.7 g |
| ferrous sulfate 7H2O | 2.79 g |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for transforming a *Zea mays* plant, said method comprising:
   (a) administering, in planta, an effective amount of a transformation-enhancing agent by injecting into said *Zea mays* plant or applying topically to said *Zea mays* plant, said transformation-enhancing agent comprising at least one component selected from the group consisting of an auxin, an auxin analog, a cytokinin, an ABA synthesis inhibitor, an antioxidant, an inhibitor of ethylene synthesis, an inhibitor of ethylene action, Medium 604, a hormone cocktail, proline mix, salts cocktail 1 and ABA;
   (b) transforming a cell from said *Zea mays* plant with a DNA construct comprising a nucleotide sequence of interest; and
   (c) regenerating a transformed *Zea mays* plant from said cell.

2. The method of claim 1 wherein said transformation-enhancing agent increases transformation efficiency.

3. The method of claim 1 wherein said cell is from an embryo produced by said plant.

4. The method of claim 3 wherein said embryo is an immature embryo.

5. The method of claim 3 wherein said administering in planta of said transformation-enhancing agent is to said plant prior to the formation of said embryo.

6. The method of claim 3 wherein said administering in planta of said transformation-enhancing agent is to said plant after the formation of said embryo.

7. The method of claim 1 wherein said transformation-enhancing agent is administered to a reproductive tissue of said plant.

8. The method of claim 1 wherein said administering in planta is to at least one part of said plant selected from a kernel, an ear, a shank, a husk, a leaf or a stem.

9. The method of claim 1 wherein said cell is a scutellar or a meristem cell.

10. A method for increasing *Zea mays* plant transformation efficiency above the level of a control, said method comprising:
  (a) administering, in planta, an effective amount of a transformation-enhancing agent by injecting into said *Zea mays* plant or applying topically to said *Zea mays* plant, said transformation-enhancing agent comprising at least one component selected from the group consisting of an auxin, an auxin analog, a cytokinin, an ABA synthesis inhibitor, an antioxidant, an inhibitor of ethylene synthesis, an inhibitor of ethylene action, Medium 604. a hormone cocktail, proline mix, salts cocktail 1 and ABA;
  (b) transforming a cell of said *Zea mays* plant with a DNA construct comprising a nucleotide sequence of interest; and
  (c) regenerating a transformed *Zea mays* plant from said cell.

11. The method of claim 10 wherein said cell is from an embryo produced by said plant.

12. The method of claim 11 wherein said embryo is an immature embryo.

13. The method of claim 11 wherein said administrating in planta of said transformation-enhancing agent to said plant is prior to the formation of said embryo.

14. The method of claim 11 wherein said administrating in planta of said transformation-enhancing agent to said plant is after the formation of said embryo.

15. The method of claim 10 wherein said transformation-enhancing agent is administered to a reproductive tissue of said plant.

16. The method of claim 10 wherein said administering in planta is to at least one part of said plant selected from a kernel, an ear, a shank, a husk, a leaf or a stem.

17. The method of claim 10 wherein said cell is a scutellar cell or a meristem cell.

18. A method for transforming a *Zea mays* plant embryo, said method comprising:
  (a) administering, in planta, an effective amount of a transformation-enhancing agent by injecting into said *Zea mays* plant or applying topically to said *Zea mays* plant, said transformation-enhancing agent comprising at least one component selected from the group consisting of an auxin, an auxin analog, a cytokinin, an ABA synthesis inhibitor, an antioxidant, an inhibitor of ethylene synthesis, an inhibitor of ethylene action, Medium 604, a hormone cocktail, proline mix, salts cocktail 1 and ABA;
  (b) transforming a cell from an embryo produced by said *Zea mays* plant with a DNA construct comprising a nucleotide sequence of interest; and
  (c) regenerating said cell into a transformed *Zea mays* embryo or a transformed *Zea mays* shoot.

19. The method of claim 18 wherein said transformation-enhancing agent increases transformation efficiency.

20. The method of claim 18 wherein said transformation-enhancing agent is administered to a reproductive tissue of said plant.

21. The method of claim 10 wherein said transformation-enhancing agent is administered to at least one part of said plant selected from the group consisting of a kernel, an ear, a shank, a husk, a leaf and a stem.

22. The method of claim 21 wherein said cell is a scutellar cell or a meristem cell.

23. The method of claim 1, 10 or 18 wherein said auxin analog is dicamba, said auxin is 2,4-D, said inhibitor of ethylene action is ACC, said inhibitor of ethylene synthesis is AVG, or said cytokinin is zeatin.

24. A method for transforming a *Zea mays* plant, said method comprising:
  (a) administering, in planta, an effective amount of a transformation-enhancing agent by injecting into said plant said transformation-enhancing agent consisting of water;
  (b) transforming a cell from said plant with a DNA construct comprising a nucleotide sequence of interest; and
  (c) regenerating a transformed plant from said cell.

* * * * *